US 6,540,399 B1

(12) United States Patent
Eppinger et al.

(10) Patent No.: US 6,540,399 B1
(45) Date of Patent: Apr. 1, 2003

(54) BITE BLOCK FOR DENTAL X-RAY PROCEDURES

(75) Inventors: Hans Eppinger, Arlington Heights, IL (US); Jerry Visak, Roselle, IL (US)

(73) Assignee: Dentsply Research & Development Corp.

( * ) Notice: Subject to any disclaimer, the term of this patent is extended or adjusted under 35 U.S.C. 154(b) by 0 days.

(21) Appl. No.: 09/543,666

(22) Filed: Mar. 30, 2000

Related U.S. Application Data

(63) Continuation of application No. 09/512,762, filed on Feb. 25, 2000
(60) Provisional application No. 60/121,783, filed on Feb. 26, 1999.

(51) Int. Cl.[7] ............................. G03B 42/02; A61B 6/14
(52) U.S. Cl. ....................... 378/170; 378/167; 378/168; 378/169
(58) Field of Search ................... 378/167, 168, 378/169, 170, 189, 191

(56) References Cited

U.S. PATENT DOCUMENTS

| | | | | |
|---|---|---|---|---|
| 1,564,269 A | * | 12/1925 | Peyser ........................ 378/162 |
| 1,571,145 A | | 1/1926 | Schlappi ..................... 378/168 |
| 1,899,877 A | | 2/1933 | Martin ........................ 378/168 |
| 2,688,096 A | | 8/1954 | Galliano et al. ............. 378/168 |
| 3,003,062 A | | 10/1961 | Updegrave ................... 378/170 |
| 3,473,026 A | | 10/1969 | Updegrave ................... 378/170 |
| 3,617,742 A | | 11/1971 | Schulman .................... 378/38 |
| 3,745,344 A | | 7/1973 | Updegrave ................... 378/170 |
| 3,777,141 A | | 12/1973 | Eggen ........................ 378/170 |
| 3,829,975 A | | 8/1974 | Balson ........................ 433/39 |
| D237,016 S | | 9/1975 | Stevenson ................... D83/1 H |
| 3,962,807 A | | 6/1976 | Pantone ...................... 40/371 |
| 4,012,638 A | | 3/1977 | Altschuler et al. .......... 378/170 |
| 4,021,672 A | | 5/1977 | Franke ........................ 378/39 |
| 4,048,506 A | | 9/1977 | Updegrave ................... 378/170 |
| 4,063,099 A | | 12/1977 | Grassme ...................... 378/39 |
| 4,097,741 A | | 6/1978 | Pfeiler et al. ................. 378/97 |
| 4,104,530 A | | 8/1978 | Weiss ......................... 378/38 |

(List continued on next page.)

FOREIGN PATENT DOCUMENTS

| | | |
|---|---|---|
| CH | 387 873 | 5/1965 |
| DE | 0 919 907 | 11/1954 |
| DE | 86 10 962 | 7/1986 |
| DE | 94 21 590 | 5/1996 |
| DE | 299 00 446 | 6/1999 |
| DE | 299 00447 | 6/1999 |
| DE | 299 0 448 | 9/1999 |
| EP | 0 080 793 | 4/1986 |
| EP | 0 379 611 | 8/1990 |
| EP | 0 247 890 | 4/1992 |
| EP | 0 733 346 | 9/1996 |
| EP | 0 626 831 | 12/1998 |
| FR | 2 602 644 | 2/1988 |
| WO | 85/00007 | 1/1985 |
| WO | 95/23554 | 9/1995 |

*Primary Examiner*—Drew A. Dunn
*Assistant Examiner*—Allen C Ho
(74) *Attorney, Agent, or Firm*—Douglas J. Hura; James B. Bieber

(57) ABSTRACT

A dental x-ray bite block (10) for securing an x-ray sensor (40) has a first block section (11) having a primary clamp face (17) and a second block section (12) having a secondary clamp face (23). The first block section (11) is configured with receiving means (41) to receive the second block section (12), such that the primary and the secondary clamp faces (17,23) are positioned in a spaced, opposing relation when the second block section (12) is received within the first block section (11). There is also stepped rachet members (50, 51) for affixing the position of the second block section (12) relative to the first block section (11) when received therein.

2 Claims, 5 Drawing Sheets

U.S. PATENT DOCUMENTS

| | | | | |
|---|---|---|---|---|
| 4,104,531 | A | 8/1978 | Weiss | 378/38 |
| 4,418,419 | A | 11/1983 | Schreiber et al. | 378/40 |
| 4,426,716 | A | 1/1984 | Muether et al. | 378/38 |
| 4,475,224 | A | 10/1984 | Grassme | 378/38 |
| 4,486,896 | A | 12/1984 | Richter et al. | 378/108 |
| 4,501,010 | A | 2/1985 | Grassme | 378/38 |
| 4,538,292 | A | 8/1985 | Linden | 378/169 |
| 4,554,676 | A | 11/1985 | Maldonado et al. | 378/170 |
| 4,598,416 | A | 7/1986 | Donato | 378/168 |
| 4,618,974 | A | 10/1986 | Grassme et al. | 378/40 |
| 4,626,216 | A | 12/1986 | Strong-Grainger | 433/229 |
| 4,805,201 | A | 2/1989 | Strong-Grainger | 378/169 |
| 4,820,152 | A | 4/1989 | Warren et al. | 433/86 |
| 4,866,750 | A | 9/1989 | Chavarria et al. | 378/168 |
| 4,941,164 | A | 7/1990 | Schuller et al. | 378/205 |
| 4,945,553 | A | 7/1990 | Willis | 378/168 |
| 4,965,885 | A | 10/1990 | Fuhrmann | 378/168 |
| 4,980,905 | A | 12/1990 | Meccariello | 378/207 |
| 5,001,738 | A | 3/1991 | Brooks | 378/170 |
| 5,044,008 | A | 8/1991 | Jackson | 378/168 |
| 5,044,009 | A | 8/1991 | Klauser | 378/168 |
| 5,090,047 | A | 2/1992 | Angotti et al. | 378/170 |
| 5,119,410 | A | 6/1992 | Donato | 378/170 |
| 5,148,032 | A | 9/1992 | Hernandez | 250/492.1 |
| 5,256,982 | A | 10/1993 | Willis | 378/168 |
| 5,289,522 | A | 2/1994 | Kanbar et al. | 378/170 |
| 5,289,919 | A | 3/1994 | Fischer | 206/571 |
| 5,327,477 | A | 7/1994 | Levy | 378/168 |
| 5,382,160 | A | 1/1995 | Shemet | 433/39 |
| 5,416,822 | A | 5/1995 | Kunik | 378/162 |
| 5,490,722 | A | 2/1996 | Sonnett et al. | 312/237 |
| 5,513,240 | A | 4/1996 | Hausmann et al. | 378/170 |
| 5,579,361 | A | 11/1996 | Augais et al. | 378/38 |
| 5,625,666 | A | 4/1997 | Willis | 378/167 |
| 5,629,972 | A | 5/1997 | Hausmann et al. | 378/170 |
| 5,652,779 | A | 7/1997 | Levy et al. | 378/170 |
| 5,666,392 | A | 9/1997 | Ploetz | 378/39 |
| 5,677,537 | A | 10/1997 | Pfeiffer | 250/370.09 |
| 5,734,693 | A | 3/1998 | Quint et al. | 378/185 |
| 5,737,388 | A * | 4/1998 | Kossila | 378/168 |
| 5,740,791 | A | 4/1998 | Aves | 128/200.26 |
| 5,751,783 | A | 5/1998 | Granfors et al. | 378/108 |
| 5,781,610 | A * | 7/1998 | Miles | 378/168 |
| 5,799,058 | A | 8/1998 | Willis et al. | 378/168 |
| 5,828,722 | A | 10/1998 | Ploetz et al. | 378/38 |
| 6,012,941 | A | 1/2000 | Burdenko et al. | 439/373 |
| 6,033,111 | A | 3/2000 | Winters et al. | 378/170 |
| 6,102,566 | A * | 8/2000 | Willis | 378/170 |
| 6,203,195 | B1 * | 3/2001 | Willis | 378/168 |

\* cited by examiner

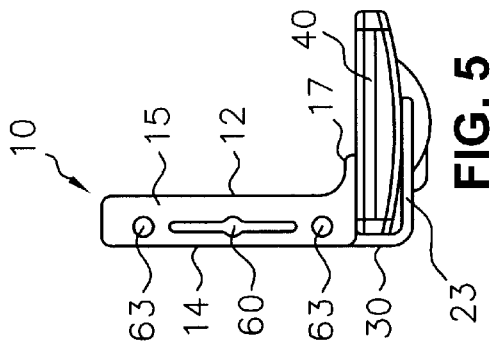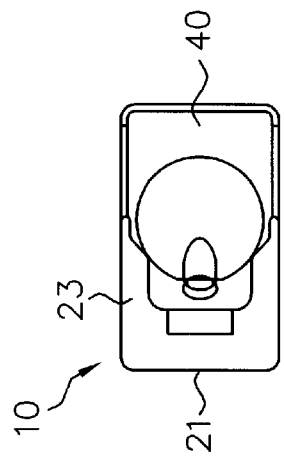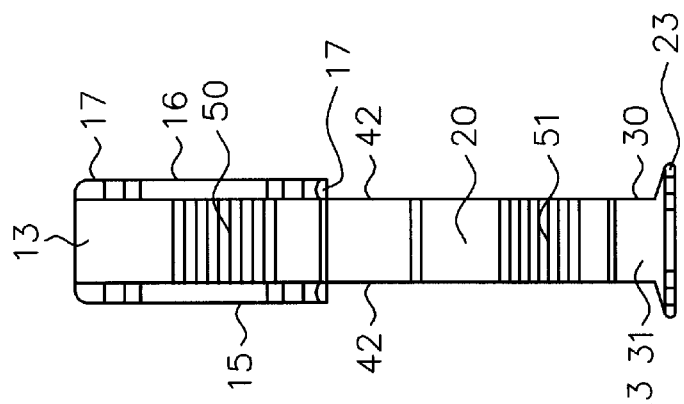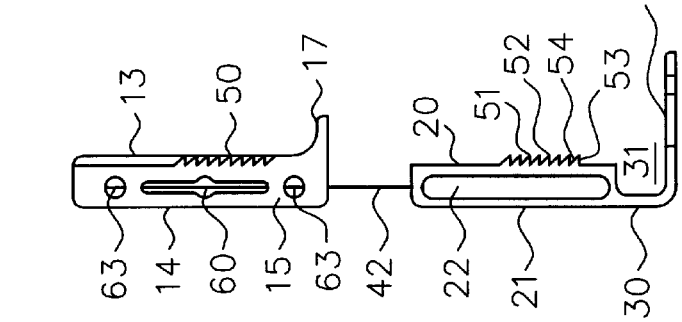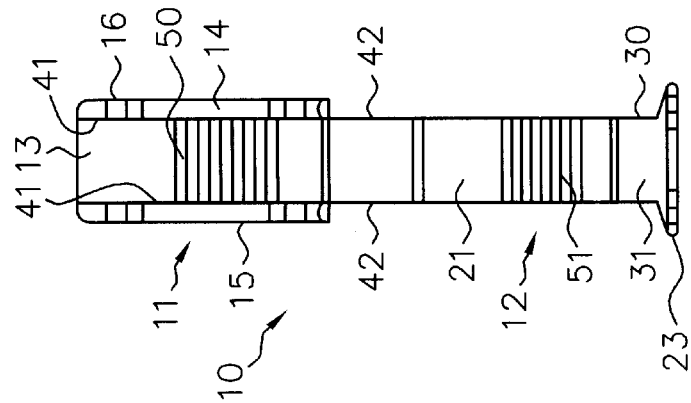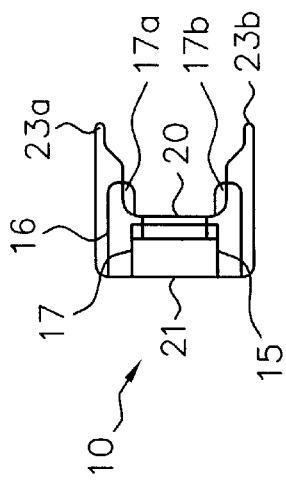

BITE BLOCK FOR DENTAL X-RAY PROCEDURES

This application is a continuation of Ser. No. 09/512,762 filed Feb. 25, 2000 which claims benefit of Provisional Application No. 60/121,783 filed Feb. 26, 1999.

TECHNICAL FIELD

The present invention is a bite block for use during dental x-ray procedures. More particularly, the invention is a bite block configured to use a variety of x-ray sensors having different widths, lengths or heights. Specifically, the invention is a bite block having at least two main parts adjustably positioned with respect to each other, such that an x-ray sensor is effectively clamped therebetween.

BACKGROUND OF THE INVENTION

Dental radiographs are made using x-ray examination units, often including an x-ray cone or tube positioned proximate the patient and aligned to take x-rays of certain teeth. Dental x-ray sensors, including films, charge coupled devices or the like, often have a generally flat or plate-like configuration and standardized dimensions so that the sensor can be placed into the oral cavity.

The sensor is placed into the patient's mouth and held in place proximate to the tooth or teeth to be examined. The x-ray's are directed through the target teeth and then through the sensor. It has been found, that proper orientation of the sensor is required to eliminate distortions and improper focus.

To ensure proper orientation of the sensor, sensor carriers or "bite blocks" have been developed. These devices often have a plate for holding the sensor and another plate that the patient bites down on to position the device and the carried sensor. A bite block is shown for example, in U.S. Pat. No. 3,473,026.

Different sensors are often used depending upon the area of the mouth to be examined. This may include for example, anterior, left, right, upper and lower bite wings, and the like. Known bite blocks have been individually designed and manufactured for each different type of sensor. The degree of secured positioning of the sensor in the holder is dictated by the dimensions of the sensor and the holder.

To enable a secure sensor position, holders are often configured to have some sort of pocket or cradle corresponding to the sensor dimensions. The user is required to physically push the sensor into the cradle. Because sensors cannot be sterilized, they have to be protected by a disposable cover prior to their insertion into the sensor holder portion of the bite block. The cover typically consists of a very thin vinyl material.

It has been found that when the covered sensor is pushed into the sensor holder, it is sometimes partially stripped of the vinyl covering. It has also been found that the cover itself sometimes prevents positive feeding of the sensor in the holder portion of the bite block.

A need exists therefore, for a sensor holder which will accommodate different sizes of sensors. A need also exists for such a sensor holder which will eliminate the problems associated with the sensor covers.

SUMMARY OF THE INVENTION

It is an object of the invention to provide a dental x-ray bite block.

It is another object of the invention to provide a bite block having an x-ray sensor holder.

It is a further object of the invention to provide a bite block having an x-ray sensor holder capable of securely holding and positioning a variety of sensors having different lengths, heights or widths.

It is yet another object of the invention to provide such a bite block which avoids the detrimental problem of stripping portions of the sensor cover when inserted into the bite block sensor holder.

These and other objects of the present invention, as well as the advantages thereof over existing art forms, which will become apparent in view of the following specification are accomplished by means hereinafter described and claimed.

In general, a dental x-ray bite block for securing an x-ray sensor, comprises a first block section having a primary clamp face; a second block section having a secondary clamp face; said first block section configured with receiving means to receive said second block section, such that said primary and said secondary clamp faces are positioned in a spaced, opposing relation when said second block section is received within said first block section; and, adjustable securing means for affixing the position of said second block section relative to said first block section when received therein.

Preferred forms of the subject dental bite block are shown by way of example in the accompanying drawings, and are deemed sufficient to effect a full disclosure of the invention. The exemplary bite block is described in detail without attempting to show all of the various forms and modifications in which the invention might be embodied; the invention being measured by the appended claims and not by the details of the specification.

BRIEF DESCRIPTION OF THE DRAWINGS

FIG. 1 is a rear elevational view of a bite block according to the invention, showing first and second block sections separated;

FIG. 2 is a side elevational view of the bite block of FIG. 1;

FIG. 3 is a front elevational view of the bite block of FIG. 1;

FIG. 4 is a top plan view of the bite block of FIG. 1, showing the second block section received within the first block section;

FIG. 5 is a side elevational view as in FIG. 4, showing the second bite block received within the first bite block and showing an sensor secured within said bite block;

FIG. 6 is a top plan view of the bite block of FIG. 4;

PREFERRED EMBODIMENTS FOR CARRYING OUT THE INVENTION

A bite block embodying the concepts of the present invention is generally designated by the number 10 on the attached drawings. It includes a first block section 11 and a second block section 12. Bite block 10 can be configured from any material conventionally used to make x-ray positioning devices, and is preferably a plastic material.

Figure 10:
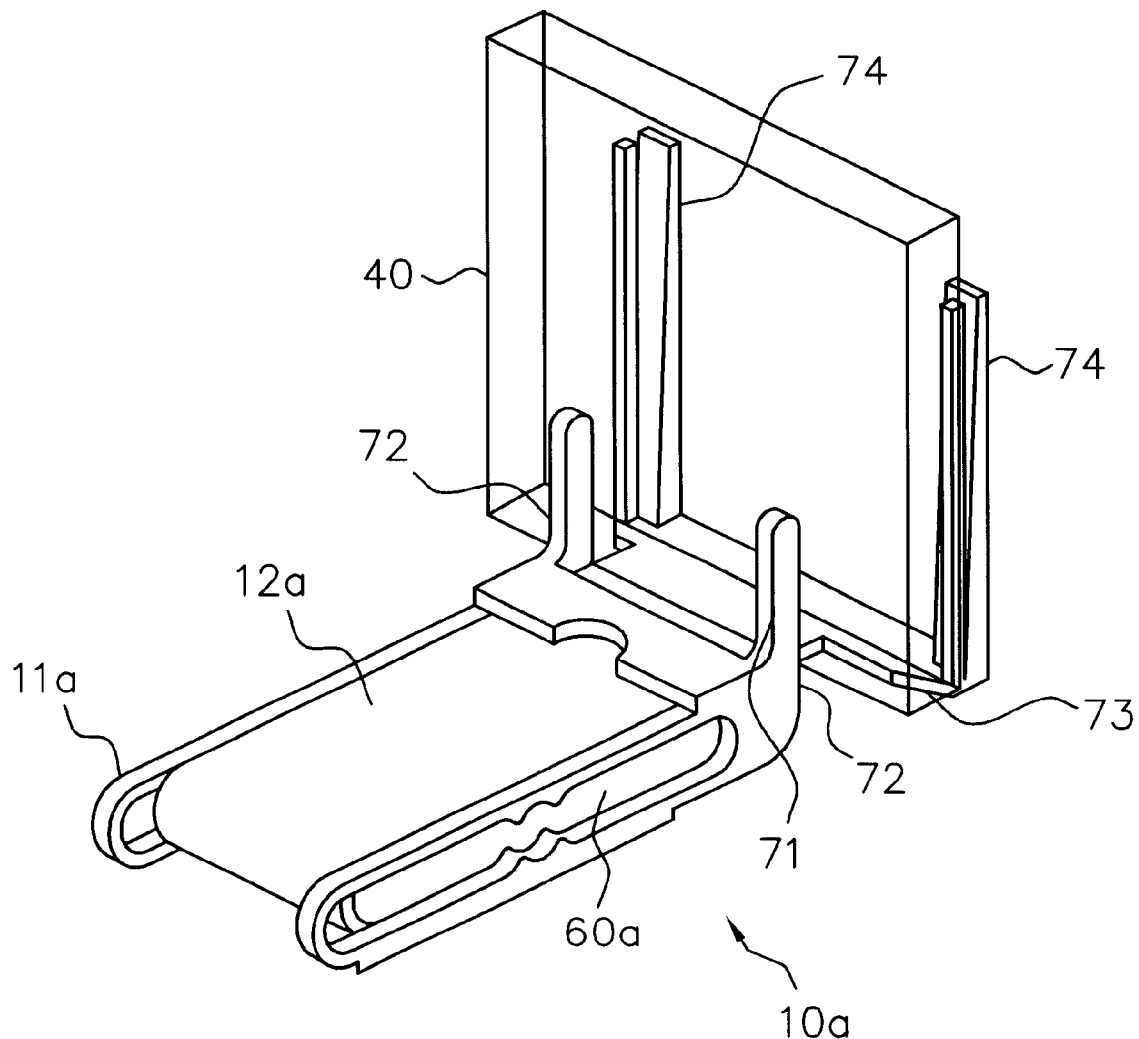
FIG. 10 is a perspective view of the bite block of 7.
Figure 11:
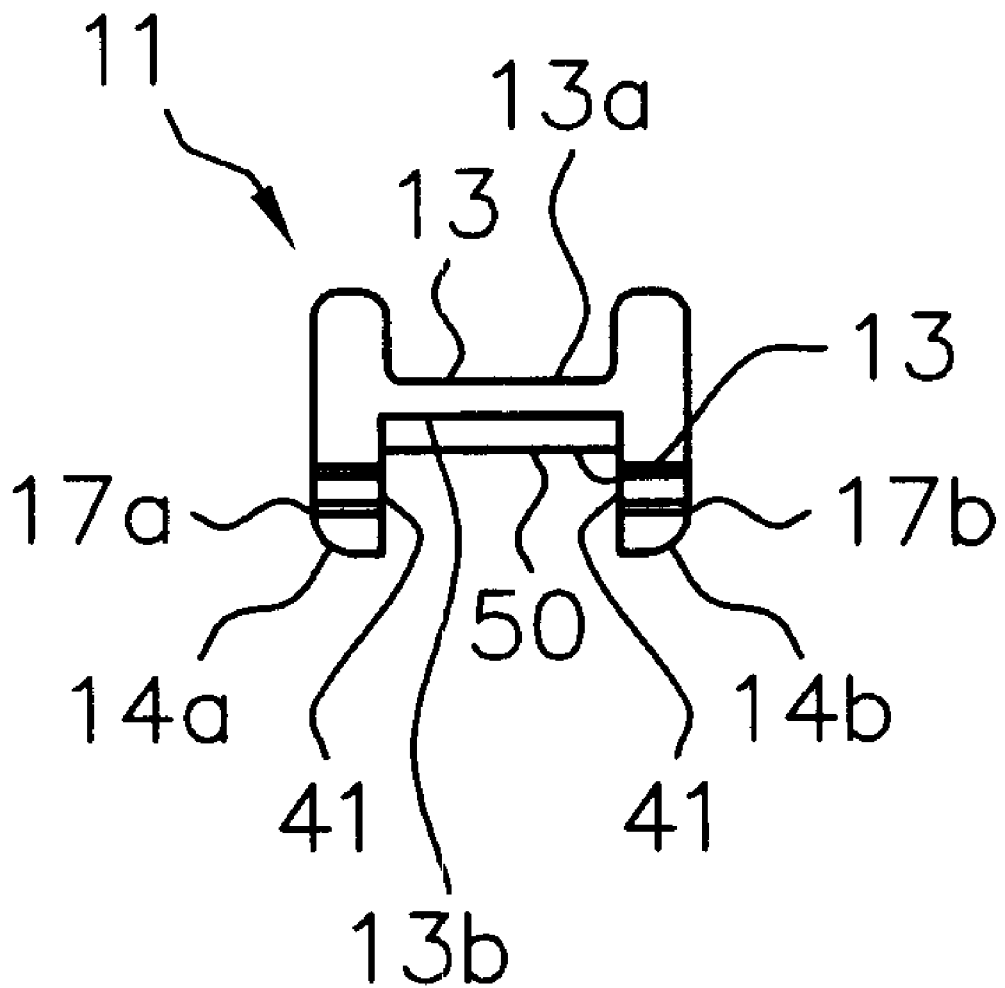
FIG. 11 is a top plan view of the first block section of the device of FIG. 1.

First block section 11 has an upstanding front wall 13 and an upstanding back wall 14 (FIGS. 1 and 10). Walls 13 and 14 are preferably arranged in a spaced, parallel arrangement (FIG. 2), such that sides 15 and 16 are positioned therebetween. As shown in FIG. 11, first block section 11 may be configured such that rear wall 14 includes wall sections 14a and 14b. Front wall 13 may also be configured to itself have a front side 13a and a rear side 13b (FIG. 11).

First block section 11 also carries a primary clamp face 17, extending from front wall 13 of first block section 11. Preferably, primary clamp face 17 extends from wall 13 of first block section 11 at a perpendicular or right angle, although any angle is within the scope of the invention. Further, primary clamp face 17 may include primary clamp face arms 17a and 17b (FIG.4).

Similarly, second block section 12 preferably has a front upstanding wall 20 and an opposing, rear upstanding wall 21. One preferred configuration of second block section 12 has a slot 22 (FIG. 2) between first and second walls 20 and 21 of second block section 12. Second block section 12 has a secondary clamp face 23 extending therefrom, preferably in a right angle to upstanding walls 20 and 21 of second block section 12. As shown in FIG. 4, secondary clamp face 23 may be comprised of separate clamp face arms 23a and 23b.

One configuration of secondary clamp face 23 extends contiguously from rear wall 21 of second block section 12 in a web 30, such that web 30 extends between secondary clamp face 23 and rear wall 21 of second block section 12. Preferably, an open or void area 31 is provided between web 30 and secondary clamp face 23. Primary and secondary clamp faces 17 and 23 are each preferably planar, although complex profiles (not shown) are within the scope of the invention.

First and second block sections 11 and 12 are configured to be removably secured to one another in an adjustable position, such that primary and secondary clamp faces 17 and 23 are in a spaced, opposing relationship. The space between primary and secondary clamp faces 17 and 23 is preferably adjustable, and once the desired position is determined and obtained, is preferably securable in that position. In this manner, clamp faces 17 and 23 can be adjusted for clamping a variety of x-ray sensors, such as exemplary sensor 40 shown in the drawings. In FIG. 5, clamp faces 17 and 23 have been adjusted to physically contact or impinge sensor 40 therebetween.

In order to effect the positioning of clamp faces 17 and 23 with respect to each other, it is preferred that one of the first and second block sections 11 and 12 is received within the other. In the embodiment of the invention shown in the drawings, second block section 12 is received within first block section 11, it being understood that the opposite arrangement is within the scope of the invention.

The receiving of secondary block section 12 within first block section 11 can be accomplished by any means. One exemplary means includes parallel, spaced and opposing channels 41 between rear walls 14a and 14b of first block section 11 (FIG. 11). Channels 41 are configured to substantially correspond dimensionally to at least one of and preferably both front and rear walls 20 and 21 of second block section 12. As shown by the directional arrows 42 in FIGS. 1–3, second block section 12 is moved toward first block section 11 and received within channels 41 thereof. Preferably, second block section 12 is movable within first block section 11, such that the movement causes the space between primary and secondary clamp faces 17 and 23 to be adjusted accordingly. It will be appreciated that primary and secondary clamp faces 17 and 23 are thereby useful for securing a sensor 40 of varying dimensions.

As stated above, it is also preferable to secure the position of primary and secondary clamp faces 17 and 23 in a desired spaced relation. Any means of accomplishing this is within the scope of the invention, including clamps, pins, screws, springs, adhesives, friction fits, or any other such means. One preferred configuration, shown on the drawings, includes stepped ratchet member 50 carried by first block section 11 and second ratchet member 51 carried by second block section 12. Each of said ratchet members 50, 51 includes a plurality of steps or teeth 52, which are substantially similar in dimension. First stepped ratchet member 50 is positioned on the rear 13b (FIG. 11) of front wall 13, such that teeth 52 extend in a direction toward rear wall 14 of first block section 11. Conversely, second ratchet member 51 is preferably carried by front wall 20 of second block section 12 and extend in a direction away from rear wall 21 of second block section 12.

Teeth 52 each have a rise 53 and a run 53 (FIG. 2). When first and second block section 11 and 12 are brought together as described above, a rise 53 of a tooth 52 of first ratchet member 50, and a rise 53 of a tooth 52 of second ratchet member 51, will each slide by an opposing tooth 52. Bite block 10 is preferably made from a plastic material, chosen in part such that at least portions of bite block 10 are substantially resilient, including teeth 52. Once at least one tooth 52 of first ratchet member 50 has been caused to slide past at least one tooth 52 of second ratchet member 51, then opposing runs 54 of the corresponding teeth 52 are caused to physically engage. This engagement substantially prevents reciprocal movement of ratchet members 50 and 51 in an opposite direction, and hence, prevents disengagement of first block section 11 and second block section 12. It is envisioned that due to its resiliency, teeth 52 may be temporarily deformed to allow reciprocal movement, but until and unless such deformation occurs, the disengagement of physically contacted opposing runs 54 is prevented. Thus, primary and secondary clamp faces 17 and 23 are locked in that position. Movement of primary clamp faces 17 and 23 towards each other is ultimately limited by physical engagement with sensor 40, thereby clamping sensor 40 therebetween.

It will be appreciated that there is nor requirement when using bite block 10 to forcefully engage sensor 40 with a preconfigured cradle. Thus the problems with previous sensor holders of the forceful engagement with a cradle are avoided.

In an alternative embodiment of the invention, bite block 10 is provided with a longitudinal through slot 60 coextensive with sides 15 and 16 and extending therebetween. It has been found that when bite block 10 is positioned within a patient's mouth, and the patient bites down on first block section 11, slot 60 increases the flexibility of first block section 11, and thereby cushions the contact between it and the patient's teeth (not shown). Slot 22 in second block section 12 may also serve this purpose.

Figure 7:
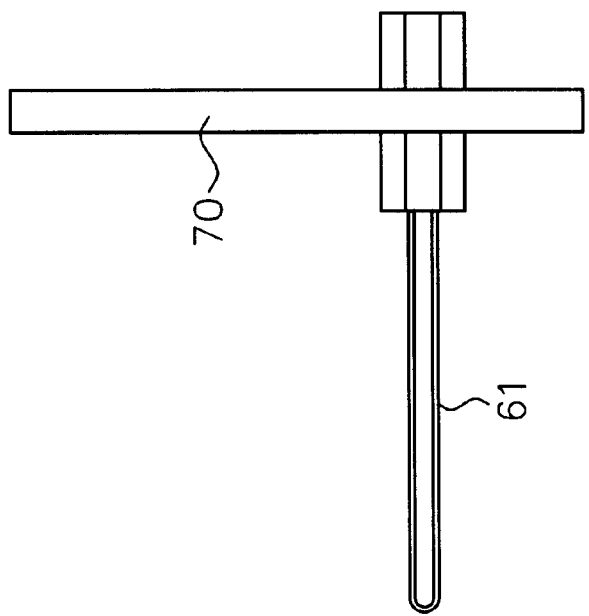
FIG. 7 is a side elevational view of an alternative embodiment of the bite block of FIG. 1, shown affixed to an x-ray positioning guide arm having a collimator ring affixed thereto.
Figure 8:
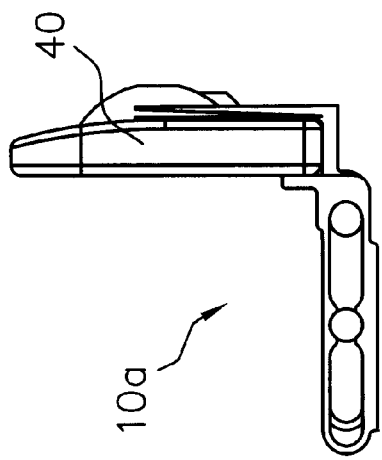
FIG. 8 is an exploded side elevational view of the guide arm shown in FIG. 7.

Bite block 10a is preferably configured to also receive a dental x-ray guide arm 61. (FIGS. 7 and 8) An exemplary guide arm, and its use with a bite block for taking a dental x-ray is shown in U.S. Pat. No. 3,473,026, which is incorporated by reference for its disclosure of a guide arm and bite block. Guide arm 61 may be therefore, conventional as known in the art. As shown in FIG. 7, guide arm 61 may be configured to be received within an x-ray tube collimator positioning ring 70 in a conventional manner. Such a ring is shown for example, in U.S. Pat. No. 3,473,026, which is incorporated by reference for its disclosure of such a ring.

Guide arm 61 according to the invention, may include pins 62 (FIG. 8) that engage pre-positioned apertures 63 (FIGS. 2 and 5) in bite block 10, in a conventional manner. Pins 62 may be affixed to guide arm 61 in any conventional manner, such as inserting pins 62 into apertures 62a in guide arm 61. Pins 62 may be integrally formed with guide arm 61, adhesive, weld or otherwise bonded to guide arm 61, or the like.

It is preferred to configure pins 62 from anodized metal such as aluminum, wherein the anodization process is preselected to provide a specified color. Thereby, the anodizing process results in a pin 62 of a preselected color. Such color selection may be used for identification purposes. Guide arm 61 may be made from a conventional material, such as stainless steel, or it too may be manufactured from an anodized, preselected color material. It is envisioned that the colors will be preselected to match the color of other components involved with the taking of an x-ray, including for example, bite block 10 or ring 70.

Figure 9:
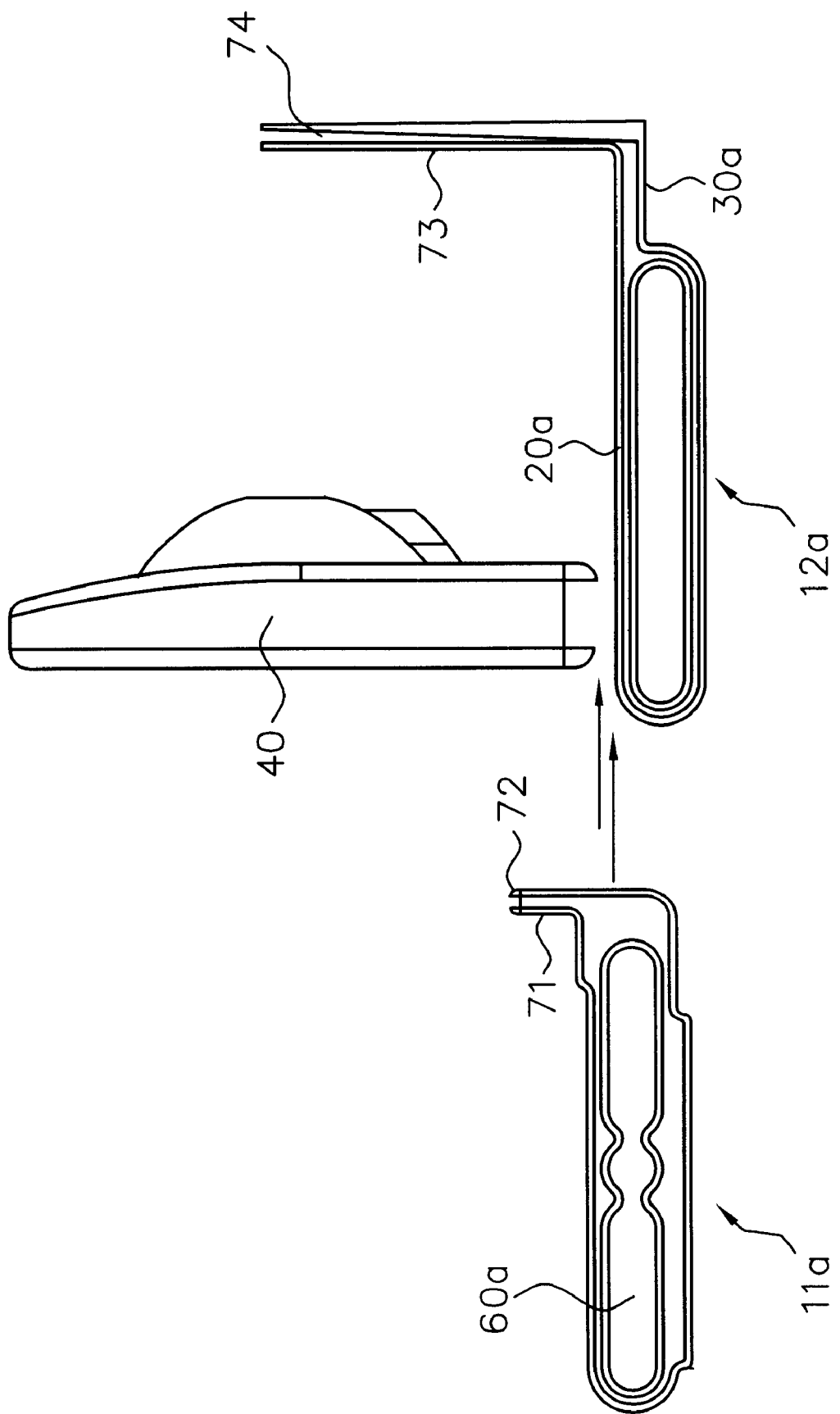
FIG. 9 is an enlarged side elevational view of the bite block of FIG. 7, shown with bite block sections disconnected and showing an x-ray sensor.

A still further embodiment of a bite block 10 is shown as block 10a in FIGS. 7, 9 and 10. In this embodiment, bite block 10a has a web 30a similar to web 30 of bite block 10. Web 30a extends from a second bite block section 12a proximate to a front wall 20a of second block section 12a. First block section 11a of bite block 10a has a through slot 60a that functions in a manner similar to slot 60 of first block section 11. Slot 60a is configured to receive pins 62 of guide arm 61, preferably in a friction fit manner.

As shown in FIG. 10, bite block 10a first block section 11a has a primary clamp face 71 having primary clamp face arms 72. Similarly, second block section 12a has a secondary clamp face 73 having secondary clamp face arms 74.

Based upon the foregoing disclosure, it should now be apparent that the use of the bite blocks described herein will carry out the objects set forth hereinabove. It is, therefore, to be understood that any variations evident fall within the scope of the claimed invention and thus, the selection of specific component elements or parts can be determined without departing from the spirit of the invention herein disclosed and described. Thus, the scope of the invention shall include all modifications and variations that may fall within the scope of the attached claims.

What is claimed is:

1. A dental x-ray bite block for securing an x-ray sensor, comprising:

a first block section having a primary clamp face;

a second block section having a secondary clamp face;

said first block section configured with receiving means to receive said second block section, such that said primary and said secondary clamp faces are positioned in a spaced, opposing relation when said second block section is received within said first block section; and, adjustable securing means for affixing the position of said second block section relative to said first block section when received therein, wherein said first block section is configured to receive an x-ray guide arm, and wherein said first block section is configured to receive an x-ray guide arm by having at least one aperture to receive at least one pin carried by said x-ray guide arm.

2. A dental x-ray guide rod for use with a bite block to position an x-ray sensor relative to a patient and an x-ray source, comprising a main body section, said main body section carrying at least one affixing pin for affixing a dental x-ray bite block in a predetermined position; said at least one affixing pin being anodized such that it has a predetermined color.

* * * * *